United States Patent
Devassy et al.

(10) Patent No.: US 12,121,887 B2
(45) Date of Patent: Oct. 22, 2024

(54) METHOD OF PREPARATION OF DEHYDROGENATION CATALYST WITH HIGH CHROMIUM CONTENT

(71) Applicant: SABIC Global Technologies B.V., Bergen op Zoom (NL)

(72) Inventors: Biju Maippan Devassy, Bangalore (IN); Rekha Mahadevaiah, Bangalore (IN); Prashant Kumar Raichur Krishtacharya, Bangalore (IN); Vinod Sankaran Nair, Bangalore (IN)

(73) Assignee: SABIC Global Technologies B.V., Bergen op Zoom (NL)

( * ) Notice: Subject to any disclaimer, the term of this patent is extended or adjusted under 35 U.S.C. 154(b) by 3 days.

(21) Appl. No.: 16/976,991

(22) PCT Filed: Feb. 22, 2019

(86) PCT No.: PCT/IB2019/051470
§ 371 (c)(1),
(2) Date: Aug. 31, 2020

(87) PCT Pub. No.: WO2019/180518
PCT Pub. Date: Sep. 26, 2019

(65) Prior Publication Data
US 2021/0001316 A1    Jan. 7, 2021

Related U.S. Application Data

(60) Provisional application No. 62/645,073, filed on Mar. 19, 2018.

(51) Int. Cl.
*B01J 37/02*    (2006.01)
*B01J 23/26*    (2006.01)
(Continued)

(52) U.S. Cl.
CPC ........... *B01J 37/0205* (2013.01); *B01J 23/26* (2013.01); *B01J 37/0236* (2013.01); *B01J 37/12* (2013.01);
(Continued)

(58) Field of Classification Search
None
See application file for complete search history.

(56) References Cited

U.S. PATENT DOCUMENTS 2,913,398 A    11/1959 Riblett et al.
3,117,169 A    1/1964 Coley et al.
(Continued)

FOREIGN PATENT DOCUMENTS

CN    101940922    1/2011
CN    102698814    10/2012
(Continued)

OTHER PUBLICATIONS

Borisevich, et al. "Dual Nanoparticle/Substrate Control of Catalytic," *Advanced Materials*, 2007, 19:2129-2133.
(Continued)

*Primary Examiner* — Coris Fung
*Assistant Examiner* — Keling Zhang
(74) *Attorney, Agent, or Firm* — Norton Rose Fulbright US LLP

(57) ABSTRACT

A method for the dehydrogenation of lower alkanes is disclosed. The method employs a chromium-alumina dehydrogenation catalyst with high chromium content supported on eta-alumina. The catalyst contains greater than 25 percent by weight chromium in the form of chromium (III) oxide, and exhibits extended stability over traditional alkane dehydrogenation catalysts.

14 Claims, 4 Drawing Sheets

(51) Int. Cl.
  B01J 37/12 (2006.01)
  B01J 37/16 (2006.01)
  C07C 5/32 (2006.01)
  B01J 21/04 (2006.01)
  C07C 11/09 (2006.01)

(52) U.S. Cl.
  CPC ............... B01J 37/16 (2013.01); C07C 5/322 (2013.01); B01J 21/04 (2013.01); C07C 11/09 (2013.01)

(56) References Cited

U.S. PATENT DOCUMENTS

| | | | |
|---|---|---|---|
| 3,346,658 | A | 10/1967 | Mulaskey et al. |
| 3,515,685 | A | 6/1970 | Hayes et al. |
| 3,692,696 | A | 9/1972 | Kravitz et al. |
| 3,723,557 | A * | 3/1973 | Hayes ............... B01J 23/6567 585/444 |
| 3,781,375 | A | 12/1973 | Shima et al. |
| 7,279,611 | B2 | 10/2007 | Alerasool et al. |
| 7,348,462 | B2 | 3/2008 | Fenouil et al. |
| 8,101,541 | B2 | 1/2012 | Fridman |
| 8,191,541 | B2 | 6/2012 | Shaffer et al. |
| 8,680,357 | B1 | 3/2014 | Rokicki et al. |
| 9,254,476 | B2 | 2/2016 | Ruettinger et al. |
| 2006/0149112 | A1 | 7/2006 | Rokicki et al. |
| 2007/0054801 | A1 | 3/2007 | Fridman et al. |

FOREIGN PATENT DOCUMENTS

| | | | |
|---|---|---|---|
| CN | 103055908 | 4/2013 | |
| CN | 103480359 | 1/2014 | |
| EP | 0947247 | 10/1999 | |
| GB | 760081 | 10/1956 | |
| GB | 942944 | 11/1963 | |
| GB | 1302223 | 1/1973 | |
| WO | WO-2014046659 A1 * | 3/2014 | ............... B01J 21/12 |

OTHER PUBLICATIONS

International Search Report and Written Opinion issued in International Patent Application No. PCT/IB2019/051470, dated Jun. 24, 2019.

Oberlander, et al. "Aluminas for Catalysts-Their Preparation and Properties," *Applied Industrial Catalysis*, 1985, 3(4).

Rashkeev, et al. "Transition metal atoms on different alumina phases: The role of subsurface sites on catalytic activity," *Physical Review B*, 2003, 67:115414.

Wefers, et al. "Oxides and hydroxides of aluminum," *Alcoa Laboratories, Alcoa Technical Paper No. 19*, 1987.

\* cited by examiner

METHOD OF PREPARATION OF DEHYDROGENATION CATALYST WITH HIGH CHROMIUM CONTENT

CROSS REFERENCE TO RELATED APPLICATIONS

This application is a national phase under 35 U.S.C. § 371 of International Application No. PCT/IB2019/051470, filed Feb. 22, 2019, which claims the benefit of priority to U.S. Provisional Patent Application Ser. No. 62/645,073, filed Mar. 19, 2018, the entire contents of each of which are hereby incorporated by reference in their entirety.

FIELD OF THE INVENTION

The invention generally concerns the production of lower olefins from the dehydrogenation of lower alkanes using a catalyst having high chromium content on an eta-alumina support.

DESCRIPTION OF RELATED ART

Alkane dehydrogenation is a commonly-employed process for production of a variety of useful unsaturated hydrocarbon products, including isobutylene for conversion to MTBE, isooctane, and alkylates to supplement and enrich gasolines. A number of catalytic processes for dehydrogenation of light alkanes are currently employed, including the CB&I CATOFIN® process, UOP's Oleflex® process, Phillips' Star™ process and the Snamprogetti-Yarsintez process.

The catalysts that are used in these processes are primarily manufactured from two different groups of materials. The CB&I CATOFIN® process and the Snamprogetti-Yarsintez process utilize chromium-alumina catalysts. In contrast, the catalysts for the UOP and Phillips processes employ catalysts comprising precious metal(s) on support.

Catalyst stability and longevity play an important role in the economics of each of the dehydrogenation processes discussed above. Because of the extreme temperatures at which the catalytic dehydrogenation reactions occur, the life expectancies of the catalysts are often limited. Improving the stability of a catalyst translates into longer catalyst life. Improved catalyst longevity reduces the rate at which catalysts must be replaced, and the down-time associated with replacing catalysts. There exists a need in the field of catalytic dehydrogenation for improving catalyst stability and concomitant catalyst longevity.

SUMMARY OF THE INVENTION

A discovery has been made that provides a solution to some of the problems discussed above. The solution is premised on the use of a catalyst having high chromium content supported on eta-alumina. The catalyst contains greater than 25 percent by weight chromium in the form of chromium (III) oxide, is provided on an eta-alumina support, and exhibits extended stability over traditional alkane dehydrogenation catalysts.

In a particular aspect of the present invention, a dehydrogenation catalyst as disclosed herein is produced by a process comprising the steps of providing an eta-alumina support, impregnating the eta-alumina support with a solution comprising at least one dissolved chromium compound, drying and calcining said impregnated support to yield a support containing less than 30 wt. % chromium (III) oxide and performing one or more additional cycles comprising each of an impregnation step, a drying step, and a calcining step to yield a dehydrogenation catalyst comprising from about 30 wt. % to about 40 wt. % chromium (III) oxide. In some aspects, the step of calcining is performed at a temperature ranging from 500° C. to 1000° C. The dehydrogenation catalyst may contain a promoter selected from the group consisting of oxides of an oxide of an alkali metal, alkaline earth metal, transition metal, or rare earth metal, and combinations of two or more thereof. In some embodiments, the promoter is a sodium compound, preferably sodium oxide. In some aspects, the dehydrogenation catalyst does not include zirconium or a zirconium compound.

In some embodiments, a method for preparing a dehydrogenation catalyst comprises the steps of providing an eta-alumina support, impregnating the eta-alumina support with a solution comprising at least one dissolved chromium compound, drying and calcining said impregnated support to yield a support containing less than 30 wt. % chromium (III) oxide, and performing one or more additional cycles comprising each of an impregnation step, a drying step, and a calcining step to yield a dehydrogenation catalyst comprising from about 30 wt. % to about 40 wt. % chromium (III) oxide. In some aspects, the step of calcining is performed at a temperature ranging from 500° C. to 1000° C. The disclosed method produces a dehydrogenation catalyst containing a promoter selected from the group consisting of an oxide of an alkali metal, alkaline earth metal, transition metal, or rare earth metal, and combinations of two or more thereof. In some embodiments, the promoter is a sodium compound, preferably sodium oxide.

In some aspects, the method and process for producing the dehydrogenation catalyst further comprise a step of modifying the eta-alumina support surface area prior to impregnation. The eta-alumina support surface area may be modified by heat-treating the eta-alumina support in the presence of a steam/air mixture or air. The eta-alumina support may be heat-treated at a temperature ranging from 350 to 700° C., preferably from 400 to 650° C., more preferably from 500 to 550° C. The eta-alumina support may be heat-treated for a period ranging from 0.5 to 6 hours, preferably from 1 to 5 hours, more preferably from 2 to 4 hours. The steam/air mixture may comprise a water flow rate ranging from 0.1 to 2.0 ml/g/hr based on the weight of the eta-alumina support, and an air flow rate ranging from 1 to 50 ml/min. In a preferred embodiment, the steam/air mixture is provided at a water flow rate of 0.5 ml/g/hr and an air flow rate of 20 ml/min.

In some aspects, a solution comprising at least one dissolved chromium compound may further comprise at least one dissolved sodium compound. The solution comprising at least one dissolved chromium compound and at least one dissolved sodium compound may be used as an initial-impregnation solution, or as a solution for subsequent impregnation of a previously-impregnated eta-alumina support material. In some embodiments, the sodium compound is sodium hydroxide.

In some embodiments, a method for the dehydrogenation of a six carbon or lower alkane comprises the steps of loading a fixed-bed reactor with a dehydrogenation catalyst produced by impregnating an eta-alumina support with a dissolved chromium compound to yield a dehydrogenation catalyst comprising from about 25 wt. % to about 40 wt. % chromium (III) oxide, passing a feed containing predominantly six carbon or lower alkanes through the reactor at a temperature sufficient to dehydrogenate said alkanes, and separating a dehydrogenated product from unreacted alkane. In some aspects, the dehydration catalyst comprises an oxide promoter, wherein the oxide promoter is selected from the group consisting of an alkali metal, alkaline earth metal, transition metal, rare earth metal, or combinations thereof. In some embodiments, the water pore volume of the eta-alumina support is more than 0.35 cm³/g. In some aspects, the method further comprises the steps of oxidizing and reducing the dehydrogenation catalyst prior to the step of passing a feed of alkanes through the reactor at a temperature sufficient to dehydrogenate the alkanes. In some embodiments, the steps of oxidizing and reducing the dehydrogenation catalyst, dehydrogenating the feed stream, and separating the dehydrogenated product are performed cyclically, that is, after the dehydrogenation, the catalyst is oxidized and reduced, and a subsequent alkane feed stream is passed over the catalyst at a temperature sufficient to dehydrogenate the alkanes. An inert gas such as nitrogen or steam may be passed through the reactor between any or all of the oxidation, reduction, and alkane dehydrogenation steps.

In some embodiments, the temperature sufficient to dehydrogenate alkanes ranges from 400 to 800° C., preferably from 500 to 750° C., more preferably from 550 to 700° C. In some aspects, passing the feed containing predominantly six carbon or lower alkanes through the reactor at a gas hourly space velocity ranging from 250 to 1,000 mlh$^{-1}$g$^{-1}$, preferably from 350 to 650 mlh$^{-1}$g$^{-1}$, more preferably from 400 to 600 mlh$^{-1}$g$^{-1}$. In some embodiments, a feed containing predominantly six carbon or lower alkanes may include butanes, such as isobutane, hexanes, pentanes, propanes, ethane, and mixtures thereof.

The following includes definitions of various terms and phrases used throughout this specification.

An alkane is defined as a linear or branched, unsubstituted or substituted, saturated hydrocarbon. Non-limiting examples of alkanes include isobutane, propane, butane, and pentane. An "alkene" is a linear or branched, unsubstituted or substituted, unsaturated hydrocarbon. Non-limiting examples of alkenes include isobutylene, propene, butylene, and pentene.

Chromium (VI) oxide and $CrO_3$ are used interchangeably herein. Chromium (III) oxide and $Cr_2O_3$ are used interchangeably herein.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %", "vol. %", or "mol. %" refers to a weight, volume, or molar percentage of a component, respectively, based on the total weight, the total volume, or total moles of a material, that includes the component. In a non-limiting example, 10 grams of component in 100 grams of the material is 10 wt. % of component.

The term "substantially" and its variations are defined to include ranges within 10%, within 5%, within 1%, or within 0.5%. By "predominantly" is meant over 50%, preferably over 60%, more preferably over 70%, and most preferably over 80%.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The methods of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the methods of the present invention are their abilities to efficiently produce lower olefins from catalytic dehydrogenation of lower alkanes.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

DETAILED DESCRIPTION OF THE INVENTION

Figure 1:
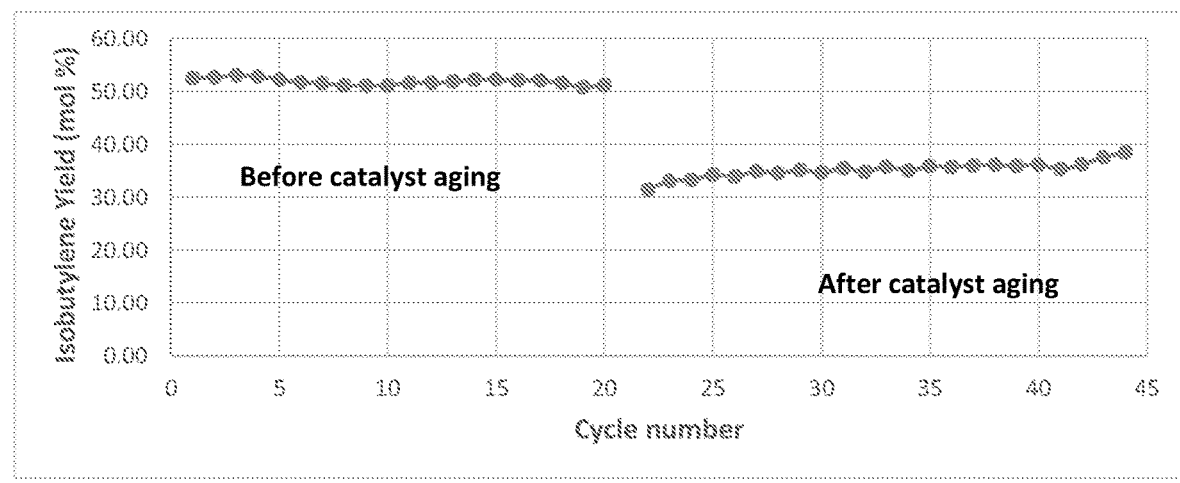
FIG. 1 is a graph comparing isobutylene yields using Comparative Catalyst 1 (20 wt. % $Cr_2O_3$ and 1 wt. % $Na_2O$ supported on eta-$Al_2O_3$) before and after an artificial accelerated-aging process.

Alkane dehydrogenation processes are reliable, proven methods for the production of olefins such as isobutylene, n-butenes, or propylene from isobutane, n-butane, or propane respectively. Alkane dehydrogenation processes typically employ fixed-bed reactors with a catalyst and operating conditions that are selected to optimize the complex relationship among conversion, selectivity and energy consumption. The high temperatures required for alkane dehydrogenation processes have an adverse effect on catalyst life. After repeated exposure to high temperatures, catalyst can deteriorate and adversely affect conversion, yield, and selectivity. The high-chromium catalysts disclosed herein represent a new class of catalyst systems having increasing catalyst longevity.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Preparation of Catalyst 1—Dual Chromium-Loading Steps

Eta-alumina extrudates (~3.1 mm×~8.9 mm) with a surface area of 335 m²/g were used for catalyst preparation. 100 g of alumina support was heat-treated in presence of a steam/air mixture in a tubular furnace at 520° C. for 1 hour (water flow rate 0.5 ml/g/hr and air flow 21 ml/min). The surface area after steam treatment was found to be 200±5 m²/g. These surface area-modified extrudates were then used for catalyst preparation by incipient wetness impregnation method.

The water pore volume of the surface area-modified extrudates was measured by taking 5 g of support and titrating it against demineralized water. The end point was the point at which the extrudates adhered to the surface of the glassware. The measurement water pore volume was determined to be 0.39±0.1 cm³/g.

First chromium-loading step: 100 ml stock solution of chromium (VI) oxide ($CrO_3$) was prepared by dissolving 85.4 g of $CrO_3$ in water. The surface area-modified support was dried at 120° C. for 2 hours prior to chromium impregnation. In the first step, 16.2 ml of stock solution was used to impregnate on 41.4 g of eta-alumina extrudates. The dried material was then calcined at 310° C. for 3 hours in presence of air (120 ml/g/hr). The water pore volume of the first impregnated material was measured by the above procedure and determined to be 0.27 cm³/g.

Second chromium-loading step: In the second step, a second 100 ml stock solution of $CrO_3$ was prepared by dissolving 54.7 g of $CrO_3$ in water. 0.77 g of NaOH was dissolved in 11 ml of the second stock solution and the resulting solution was used for the second impregnation. The second impregnation was carried out by contacting the second impregnation solution with the first impregnated material at room temperature.

The impregnated alumina support was then kept at room temperature for 2 hours then dried at 120° C. in a muffle furnace for 12 hours. The dried sample was calcined at 650° C. for 2 hours under air atmosphere (240±5 ml/g/hr), followed by heating at 750° C. for 4 hours under a 80% air and 20% steam environment (total flow rate 240±5 ml/g/hr).

After calcination, the catalyst was cooled in the presence of air then stored in an air-tight container. The final surface area of the catalyst after calcination was found to be 92 m²/g the catalyst. The final composition of the catalyst corresponds to chromium (III) oxide ($Cr_2O_3$)—30 wt. %, $Na_2O$—1 wt. %, with the balance corresponding to $Al_2O_3$. The chromium content in the catalyst is expressed, calculated as chromium (III) oxide ($Cr_2O_3$).

Example 2

Preparation of Catalyst 1—Single Chromium-Loading Step

In attempting to prepare a catalyst having the same composition as the catalyst of Catalyst 1 via a single impregnation step method, 100 ml stock solution of $CrO_3$ was prepared by dissolving 146.7 g of $CrO_3$ in water. However, this solution is found to be highly viscous and could not be used for uniform impregnation of chromium on eta-alumina.

Example 3

Preparation of Comparative Catalyst 1—Single Chromium-Loading Step

Eta-alumina extrudates (~3.1 mm×~8.9 mm) with a surface area of 335 m²/g were used for catalyst preparation. 100 g of alumina support was heat-treated in presence of a steam/air mixture in a tubular furnace at 550° C. for 3 hours (water flow rate 0.5 ml/g/hr and air flow 21 ml/min). The surface area after steam treatment was found to be 160±5 m²/g. These surface area-modified extrudates were then used for catalyst preparation by incipient wetness impregnation method.

The water pore volume of the surface area-modified extrudates was measured by titrating 5 grams of support against demineralized water. Titration end point was reached when the last addition of water caused the extrudates to stick together or adhere to the surface of the glassware (Some Physical measurements on catalysts and their significance by R. M Engelbrecht from Monsanto Chemical Company, Page 27). The water pore volume was determined to be 0.39±0.1 cm³/g.

A 100 ml stock solution of $CrO_3$ was prepared by dissolving 85.4 g of $CrO_3$ in water. The impregnation solution was prepared by dissolving 0.77 g of NaOH in 18.5 ml of stock solution. The surface area-modified support was dried at 120° C. for 2 hours prior to chromium impregnation. The impregnation was carried out by contacting the impregnation solution with 47.40 g of surface area-reduced eta-alumina support at room temperature.

The impregnated alumina support was then kept at room temperature for 2 hours and then dried at 120° C. in a muffle furnace for 12 hours. The dried sample was then calcined at 650° C. for 2 hours under air atmosphere (flow rate, 240±5 ml/min). After 2 hours, the temperature was increased to 750° C. and the sample was further calcined for 4 hours under a 80% air and 20% steam environment (total flow rate 240±5 ml/g/hr). After calcination, the catalyst was cooled in presence of air then stored in an air-tight container. The final surface area of the catalyst was found to be 86 m²/g. The final composition of the catalyst was $Cr_2O_3$—20 wt. %, $Na_2O$—1 wt. %, with the balance corresponding to $Al_2O_3$.

Catalyst Testing

The dehydrogenation activity of Catalyst 1 (inventive catalyst) and Comparative Catalyst 1 were measured in a tubular fixed-bed quartz reactor. Catalyst loading and reactor details were as follows: catalyst weight=5 g, catalyst particle size=0.4-0.5 mm, reactor ID=16 mm, reactor OD=19 mm.

Isobutane (99.9 vol. %) was used as a reactor feed. Quartz chips having a size of 1-1.4 mm were loaded above the catalyst bed. A nitrogen purge was employed between the steps of dehydrogenation, catalyst regeneration/oxidation, and reduction with hydrogen. The total feed flow in the dehydrogenation step corresponds to a gas hourly space velocity (GHSV)=600 mlh$^{-1}$g$^{-1}$. The reactor outlet gases were analyzed by online gas chromatograph (Agilent 6890) equipped with a flame ionization detector for hydrocarbon analysis and thermal conductivity detector for hydrogen analysis. The reactant and products flow rates were measured using Ritter type wet gas flow meter.

The reactor was operated at atmospheric pressure and in a cyclic mode with the following steps: 1) oxidize in air at 650° C., 30 min; 2) purge with nitrogen at 650° C., 10 min.; 3) reduce with H$_2$ at 650° C., 6 min.; 4) cooling with nitrogen from 650° C. to 585° C., 40 min. hold at 585° C.; 5) dehydrogenate isobutane at 585° C., 21 min.; and 6) analyze with gas chromatograph (GC) at 20th minute from the start of the isobutane feed. Steps 1 through 6 were repeated several times.

Catalyst Stability Evaluation

Catalyst stability evaluation was carried out by an artificial accelerated-aging procedure in a cyclic mode of operation. The cycle consisted of reduction-dehydrogenation-oxidation stages with suitable time intervals. The aging was carried out at 820° C. for 72 hours. Catalyst stability evaluation parameters included a catalyst weight=5 g, isobutene GHSV=400 mlg$^{-1}$h$^{-1}$, and an air to isobutane volume ratio of 4. The following steps were performed: 1) oxidize in air for 15 min.; 2) purge with nitrogen for 3 min.; 3) reduce with H$_2$ for 6 min.; 4) purge with nitrogen for 3 min.; 5) iso-butane flow for 3 min.; and 6) purge with nitrogen for 3 min.

Results

Non-limiting aspects of the present invention are discussed in further detail below with reference to the figures.

Isobutylene Selectivities for Pre-Aged Catalyst 1 and Comparative Catalyst 1

Figure 2:
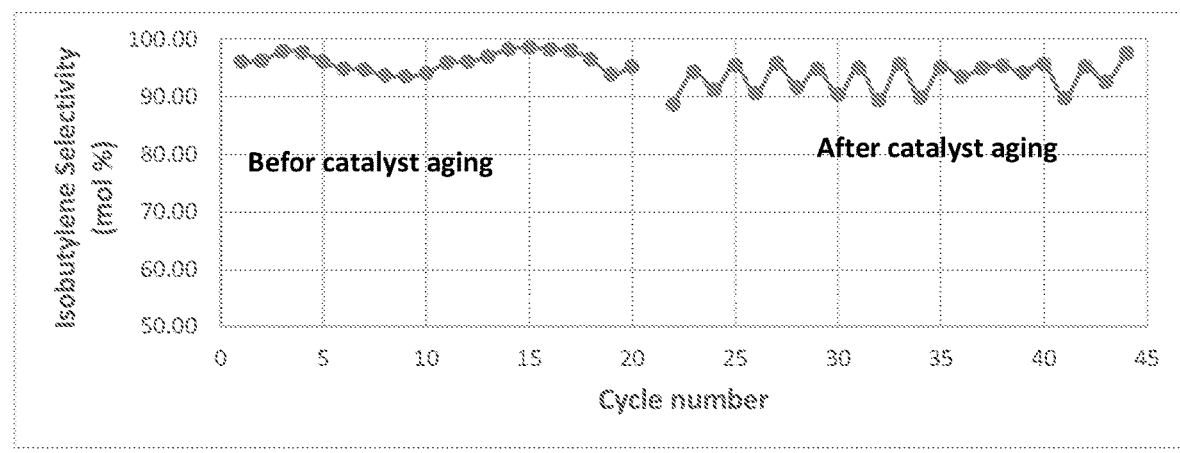
FIG. 2 is a graph comparing isobutylene selectivities using Comparative Catalyst 1 (20 wt. % $Cr_2O_3$ and 1 wt. % $Na_2O$ supported on eta-$Al_2O_3$) before and after an artificial accelerated-aging process.
Figure 4:
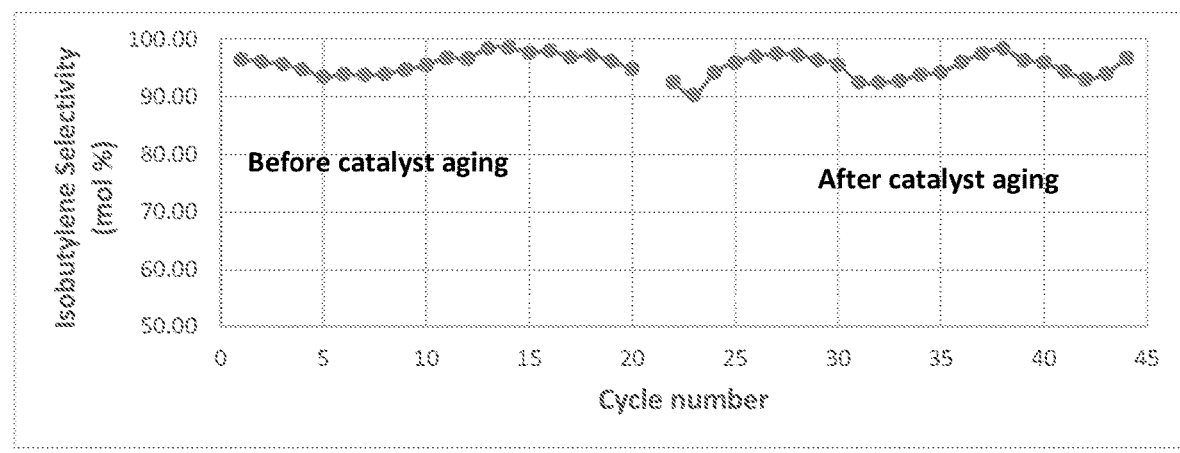
FIG. 4 is a graph comparing isobutylene selectivities using Catalyst 1 (30 wt. % $Cr_2O_3$ and 1 wt. % $Na_2O$ supported on eta-$Al_2O_3$) before and after an artificial accelerated-aging process.

In comparing isobutylene selectivities obtained from the use of pre-aged Catalyst 1 and Comparative Catalyst 1 (FIG. 2 and FIG. 4, left side), both catalysts lead to an isobutylene selectivity of ~96%.

Isobutylene Selectivities for Post-Aged Catalyst 1 and Comparative Catalyst 1

In comparing isobutylene selectivities obtained from the use of post-aged Catalyst 1 and Comparative Catalyst 1 (FIG. 2 and FIG. 4, right side), both catalysts lead to an isobutylene selectivity of ~94%.

Isobutylene Yields for Pre-Aged Catalyst 1 and Comparative Catalyst 1

Figure 3:
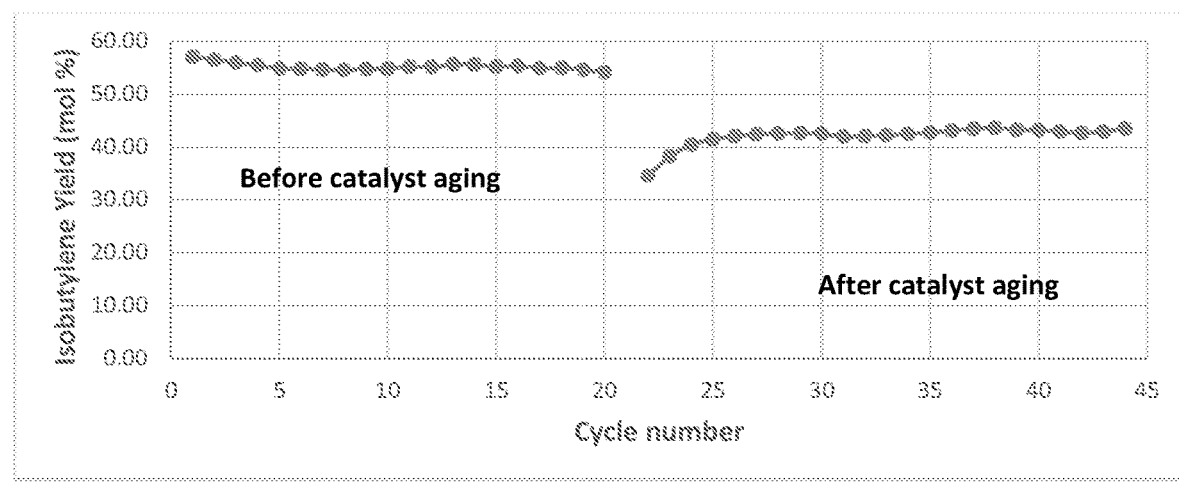
FIG. 3 is a graph comparing isobutylene yields using Catalyst 1 (30 wt. % $Cr_2O_3$ and 1 wt. % $Na_2O$ supported on eta-$Al_2O_3$) before and after an artificial accelerated-aging process.

In comparing isobutylene yields obtained from the use of pre-aged Catalyst 1 and Comparative Catalyst 1 (FIG. 1 and FIG. 3, left side), the inventive catalyst (Catalyst 1) exhibits improved isobutylene yield over Comparative Catalyst 1 (~56% versus ~51%).

Isobutylene Yields for Post-Aged Catalyst 1 and Comparative Catalyst 1

In comparing the post-aged variants (FIG. 1 and FIG. 3, right side), it is clear that Catalyst 1 (30 wt. % Cr$_2$O$_3$) is more stable than Comparative Catalyst 1 (20 wt. % Cr$_2$O$_3$). The isobutylene yield for post-aged Comparative Catalyst 1 was reduced to ~35%, whereas the isobutylene yield obtained from using post-aged Catalyst 1 was significantly higher (~43%).

The results above demonstrate that the high-chromium catalysts of the present invention exhibit improved isobutylene yields over a comparable catalyst having lower chromium loading. The high-chromium catalysts of the present invention are significantly more resistant to aging-induced catalyst degradation and reduction of activity. In response to an artificial accelerated-aging procedure, the high-chromium loading catalysts of the present invention exhibited significantly higher isobutylene yields than a comparable catalyst having lower chromium loading. Together, the experimental results demonstrate that the high-chromium loading catalysts of the present invention provide improved yields and are more resistant to degradation over time.

In the context of the present invention, embodiments 1-14 are described. Embodiment 1 is a dehydrogenation catalyst. The catalyst is produced by a process which includes: (a) providing an eta-alumina support; (b) impregnating the eta-alumina support with a solution comprising at least one dissolved chromium compound; (c) drying and calcining the impregnated support to yield a support containing less than 30 wt. % chromium (III) oxide; and (d) performing one or more additional cycles including each of an impregnation step, a drying step, and a calcining step to yield a dehydrogenation catalyst containing from about 30 wt. % to about 40 wt. % chromium (III) oxide. The dehydrogenation catalyst contains a promoter selected from the group consisting of an oxide of an alkali metal, alkaline earth metal, transition metal, or rare earth metal, and combinations of two or more thereof. Embodiment 2 is the catalyst of embodiment 1, wherein the step of impregnating includes impregnating with a solution including at least one dissolved chromium compound and at least one dissolved sodium compound. Embodiment 3 is the catalyst of either of embodiments 1 or 2, wherein the step of performing one or more additional cycles includes impregnating with a solution including at least one dissolved chromium compound and at least one dissolved sodium compound. Embodiment 4 is the catalyst of either of embodiments 2 or 3, wherein at least one dissolved sodium compound is sodium hydroxide.

Embodiment 5 is a method of preparing a dehydrogenation catalyst. The method includes: (a) providing an eta-alumina support; (b) impregnating the eta-alumina support with a solution comprising at least one dissolved chromium compound; (c) drying and calcining said impregnated support to yield a support containing less than 30 wt. % chromium (III) oxide; and (d) performing one or more additional cycles comprising each of an impregnation step, a drying step, and a calcining step to yield a dehydrogenation catalyst containing from about 30 wt. % to about 40 wt. % chromium (III) oxide. The method produces a dehydrogenation catalyst containing a promoter selected from the group consisting of an oxide of an alkali metal, alkaline earth metal, transition metal, or rare earth metal, and combinations of two or more thereof. Embodiment 6 is the method of embodiment 5, wherein the step of impregnating includes impregnating with a solution including at least one dissolved chromium compound and at least one dissolved sodium compound. Embodiment 7 is the method of either of embodiments 5 or 6, wherein the step of performing one or more additional cycles includes impregnating with a solution including at least one dissolved chromium compound and at least one dissolved sodium compound. Embodiment 8 is the method of either of embodiments 6 or 7, wherein at least one dissolved sodium compound is sodium hydroxide.

Embodiment 9 is a method for the dehydrogenation of a six carbon or lower alkane. The method includes: (a) loading a fixed-bed reactor with a dehydrogenation catalyst produced by impregnating an eta-alumina support with a dissolved chromium compound to yield a dehydrogenation catalyst containing from about 30 wt. % to about 40 wt. % chromium (III) oxide, wherein the water pore volume of the eta-alumina support is more than 0.35 cm$^3$/g; (b) passing a feed containing predominantly six carbon or lower alkanes through the reactor at a temperature sufficient to dehydrogenate said alkanes; and (c) separating a dehydrogenated product from unreacted alkane. Embodiment 10 is the method of embodiment 9, wherein the dehydration catalyst is composed of an oxide promoter, wherein the oxide promoter is selected from the group consisting of an alkali metal, alkaline earth metal, transition metal, rare earth metal, or combinations thereof. Embodiment 11 is the method of either of embodiment 9 or 10, including the steps of oxidizing and reducing the dehydrogenation catalyst prior to step (b) above. Embodiment 12 is the method of embodiment 11, including cyclically repeating the steps of oxidizing and reducing the dehydrogenation catalyst, dehydrogenating the feed stream, and separating the dehydrogenated product. Embodiment 13 is the method of any of embodiments 9 to 12, wherein the temperature sufficient to dehydrogenate alkanes ranges from 400 to 800° C. Embodiment 14 is the method of any of embodiments 9 to 13, wherein passing the feed containing predominantly six carbon or lower alkanes through the reactor is performed at a gas hourly space velocity ranging from 250 to 1,000 mlh$^{-1}$g$^{-1}$. Embodiment 15 is the method of any of embodiments 9 to 14, wherein the feed containing predominantly six carbon or lower alkanes comprises isobutane.

The invention claimed is:

1. A dehydrogenation catalyst produced by a process comprising:
    (a) preparing a heat-treated eta-alumina support by heat-treating an eta-alumina having a surface area in the presence of a steam and air mixture to form the heat-treated eta-alumina support;
    (b) impregnating the heat-treated eta-alumina support with a solution comprising at least one dissolved chromium compound and a promoter to yield an impregnated support;
    (c) drying and calcining said impregnated support to yield a calcined impregnated support containing less than 30 wt. % chromium (III) oxide based on the total weight of the calcined impregnated support;
    (d) performing one or more additional cycles comprising each of the impregnating step, the drying step, and the calcining step to yield a dehydrogenation catalyst containing only the eta-alumina support, the promoter, and from 25 wt. % to about 40 wt. % chromium (III) oxide based on the weight of the dehydrogenation catalyst;
    wherein the promoter is selected from the group consisting of an alkali metal oxide, an alkaline earth metal oxide, a transition metal oxide and a rare earth metal oxide, and combinations of two or more thereof; and
    wherein a water pore volume of the heat-treated eta-alumina support is more than 0.35 cm$^3$/g.

2. The dehydration catalyst of claim 1, wherein the promoter comprises a sodium compound.

3. The dehydration catalyst of claim 1, wherein the step of performing one or more additional cycles comprises impregnating with the solution comprising the at least one dissolved chromium compound and the promoter, wherein the promoter comprises a sodium compound.

4. The dehydration catalyst of claim 1, wherein the dissolved promoter is sodium hydroxide.

5. The dehydrogenation catalyst of claim 1, wherein the dehydrogenation catalyst comprises from 30 wt. % to about 40 wt. % chromium (III) oxide based on the weight of the dehydrogenation catalyst.

6. The dehydrogenation catalyst of claim 1, wherein the dehydrogenation catalyst comprises 40 wt. % chromium (III) oxide, based on the weight of the dehydrogenation catalyst.

7. A method of preparing a dehydrogenation catalyst according to claim 1, comprising:
    (a) preparing a heat-treated eta-alumina support by heat-treating eta-alumina having a surface area in the presence of a steam and air mixture to form the heat-treated eta-alumina support;
    (b) impregnating the heat-treated eta-alumina support with a solution comprising at least one dissolved chromium compound to yield an impregnated support;
    (c) drying and calcining said impregnated support to yield a support containing less than 30 wt. % chromium (III) oxide;
    (d) subjecting the support containing less than 30 wt. % chromium (III) oxide to one or more additional cycles comprising each of an impregnation step, a drying step, and a calcining step to yield the dehydrogenation catalyst, wherein the dehydrogenation catalyst contains from about 30 wt. % to about 40 wt. % chromium (III) oxide.

8. A method for the dehydrogenation of a six carbon or lower alkane comprising:
    (a) loading a fixed-bed reactor with the dehydrogenation catalyst according to claim 1;
    (b) passing a feed containing predominantly six carbon or lower alkanes through the reactor at a temperature sufficient to dehydrogenate said alkanes; and
    (c) separating a dehydrogenated product from unreacted alkane.

9. A dehydrogenation catalyst comprising:
    (a) a heat-treated eta-alumina support impregnated with chromium (III) oxide and a promoter,
    wherein the dehydrogenation catalyst comprises from 25 wt. % to about 40 wt. % of the chromium (III) oxide based on the weight of the dehydrogenation catalyst;
    wherein the promoter is selected from the group consisting of an alkali metal oxide, an alkaline earth metal oxide, a transition metal oxide and a rare earth metal oxide, and combinations of two or more thereof;
    wherein a water pore volume of the heat-treated eta-alumina support is more than 0.35 cm$^3$/g;
    wherein the heat-treated eta-alumina support is prepared by heat-treating eta-alumina having a surface area in the presence of a steam and air mixture to form the heat-treated-eta-alumina support.

10. The dehydrogenation catalyst of claim 9, containing from 30 wt. % to about 40 wt. % chromium (III) oxide based on the weight of the dehydrogenation catalyst.

11. The dehydrogenation catalyst of claim 9, wherein the promoter comprises an alkaline earth metal oxide.

12. The dehydrogenation catalyst of claim 9, wherein the promoter comprises a transition metal oxide.

13. The dehydrogenation catalyst of claim 9, wherein the promoter comprises a rare earth metal oxide.

14. The dehydrogenation catalyst of claim 9, wherein the heat-treated-eta-alumina support is an extrudate.

\* \* \* \* \*